United States Patent [19]

Kao et al.

[11] 4,374,254

[45] Feb. 15, 1983

[54] PROCESS FOR PRODUCING SUBSTITUTED PYRROLES

[75] Inventors: James T. F. Kao; Wayne D. Jensen, both of Baton Rouge, La.

[73] Assignee: Ethyl Corporation, Richmond, Va.

[21] Appl. No.: 228,174

[22] Filed: Jan. 23, 1981

[51] Int. Cl.$^3$ .......................................... C07D 207/323
[52] U.S. Cl. .................................... 548/527; 548/539
[58] Field of Search .................... 260/326.47, 326.35

[56] References Cited

U.S. PATENT DOCUMENTS 3,752,826  8/1973  Carson ........................... 260/326.47
3,952,012  4/1976  Carson ........................... 260/326.47

OTHER PUBLICATIONS

Vogel; Practical Organic Chemistry, 1957, p. 151.

*Primary Examiner*—Mary C. Lee
*Attorney, Agent, or Firm*—Donald L. Johnson; John F. Sieberth; James M. Pelton

[57] ABSTRACT

A process for preparing 5-aroylpyrrole compounds and recovering them from crude solutions by extracting with a mixed organic extractant such as an aromatic hydrocarbon-alkanol mixture followed by aqueous extraction with a base, decolorizing, and recovering the 5-aroylpyrrole compound for final purification.

10 Claims, No Drawings

PROCESS FOR PRODUCING SUBSTITUTED PYRROLES

BACKGROUND OF THE INVENTION

This invention relates to a process for producing 5-aroylpyrrole compounds, particularly 5-aroylpyrrole-2-acetic acid compounds and derivatives thereof which are known in the art as having anti-inflammatory and analgesic actions.

5-Aroylpyrrole compounds and substituted 5-aroylpyrrole-2-acetic acid compounds, particularly those substituted with a lower alkyl group in the 1- and 4-positions are known in the prior art, see Carson, U.S. Pat. No. 3,752,826. A number of compounds in this class of 5-aroylpyrrole alkanoic acids and the corresponding acid derivatives thereof are taught in this patent.

U.S. Pat. No. 3,952,012 teaches the process for making a lower alkyl 5-aroyl-1-$R_4$-4-$R_5$-pyrrole-2-acetate by a process which comprises hydrolyzing a lower alkyl 1-$R_4$-4-$R_5$-3-lower alkoxy carbonyl pyrrole-2-acetate under alkaline conditions to the diacid, partially re-esterifying the pyrrole diacid to the lower alkyl 1-$R_4$-4-$R_5$-3-carboxypyrrole-2-acetate by treating the pyrrole diacid with an acidic solution of a lower alkanol, decarboxylating the 3-carboxy group of the partially re-esterified pyrrole acid ester by heating to carbon dioxide elimination temperatures and then acylating the pyrrole monoester to a lower alkyl 5-aroyl-1-$R_4$-4-$R_5$-pyrrole-2-acetate by treatment with an aroyl chloride in the presence of a Lewis Acid in an organic solvent suitable for a Friedel-Crafts acylation. The examples of U.S. Pat. No. 3,952,012 teach recovery of the desired 1,4-dimethyl-5-(p-toluoyl)-pyrrole-2-acetic acid by precipitation of a solid from dilute acetic aqueous solution, collecting the precipitate, drying in vacuo and recrystallizing to obtain a white solid. This procedure requires solids handling which is difficult in large scale operations and results in losses of expensive pharmaceutical materials which is equally undesirable.

However, as shown in the prior art, because methods of producing the 1,4-dilower alkyl substituted 5-aroylpyrrole alkanoic acids involve multi-step, complex process steps, there are opportunities for impurities, degradation products and undesirable by-product materials to be present. Without specific purification steps, these undesirables may not be removed from the process and, in fact may be carried forward with the final product. Further, because the desired compounds are useful as pharmaceutical agents and intermediates therefor, it is economically and therapeutically favored to produce only the acceptable pharmaceutically efficacious agent, or intermediate therefor, and obtain that in as pure form as possible with as high a yield as possible. In many instances, the by-products are carried along with the desired 5-aroylpyrrole compounds and this presents problems of recovery and separation of the desired 1,4-dilower alkyl 5-aroylpyrrole-2-acetic acid or corresponding acid derivatives thereof.

Accordingly, one objective of the present invention is to overcome the problem of handling expensive pharmaceutical reagents as solids with the resultant losses. Another objective is to provide conversion to the desired form in a manner to minimize material losses and separate from impurities. These and other objectives will be accomplished by the process of the present invention as described in more detail hereinafter.

SUMMARY OF THE INVENTION

The present invention provides a process for preparing a substituted pyrrole compound of the general formula

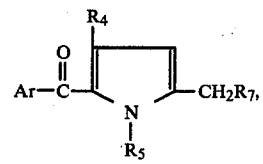

wherein the foregoing formula, said $R_4$ and $R_5$ each are independently selected from loweralkyl, and said $R_7$ is COOM in which M is an alkali metal, and Ar is selected from phenyl, thienyl, 5-methylthienyl, monosubstituted phenyl and polysubstituted phenyl, each substituent of said substituted phenyls being a member selected from the group consisting of halo, loweralkyl, trifluoromethyl, loweralkoxy, nitro, amino, cyano and methylthio, which comprises the steps of (a) treating a crude aqueous mixture containing a 1-$R_5$-4-$R_4$-5-aroylpyrrole-2-acetic acid with a mixed organic extractant therefor so that the pyrrole is extracted into the organic phase, (b) separating the phases, (c) treating the organic phase with a basic aqueous extractant so that the pyrrole salt formed is extracted into the aqueous phase, (d) separating the phases, (e) contacting the pyrrole with a decolorizing agent and (f) recovering the resulting substituted pyrrole compound of general formula above.

The starting material which is a 5-aroylpyrrole-2-acetic acid is more fully described in Carson U.S. Pat. Nos. 3,752,826 and 3,952,012, both of which references are incorporated herein by reference as if fully set forth. More particularly, the starting pyrrole is a 1,4-di-loweralkyl-5-aroylpyrrole-2-acetic acid. Particularly preferred as the desired end product is the alkali metal salt and, more specifically, the sodium salt. The preferred aroyl groups include toluoyl, chlorobenzoyl and the like, all as more specifically disclosed in the Carson references. The starting pyrrole compound may be in solution with an organic solvent or may be neat, that is to say without any solvent. More preferably, however, the starting pyrrole is in an aqueous mixture from the acidification of a saponified acylated pyrrole monoester. Usually, the pyrrole compound will be in admixture with various impurities and color-forming bodies, both in varying amounts, and have a number of by-products and degradation products therewith which are associated with the process for preparation. In the conventional manner of product pyrrole purification, a precipitate is formed and impurities remain in the aqueous solution. However, this requires filtration or decantation of the liquid from the solid product precipitate which tends to leave some impurities in the product.

The present process provides a liquid extraction system whereby the desired pyrrole product is extracted from an aqueous phase to an organic phase and then back to an aqueous phase for subsequent recrystallization as a final purification. In accord with the present process, the aroyl pyrrole salt is treated with an organic extractant which is selected from an organic hydrocarbon compound selected from benzene, xylene and toluene which organic hydrocarbon compound is in admixture with a lower alkanol to increase the solubility of the pyrrole in the organic hydrocarbon. The lower alkanol is selected from methanol, ethanol and propanol. It is only required that the mixed organic extractant system contact the crude aqueous pyrrole mixture containing the 5-aroylpyrrole-2-acetic acid and the system is agitated at a convenient temperature, such as a temperature ranging from 75° to 100° C.

More preferably, the mixed organic extractant is a mixture of xylene and ethanol and, most preferably, the mixed organic extractant contains from 75 to about 95 wt. percent of the organic hydrocarbon compound and from about 5 to about 25 wt. percent of the lower alkanol. In a most highly preferable embodiment, the mixed organic extractant contains 90 percent xylene and 10 percent ethanol. Following extraction of the pyrrole-2-acetic acid compound from the aqueous phase into the organic phase, the phases are separated and the aqueous phase containing impurities is discarded or treated prior to discarding. The organic phase containing the desired pyrrole-2-acetic acid is then treated with a basic aqueous extractant forming the pyrrole-2-acetic acid salt which is extracted into the aqueous phase. The aqueous phase is made basic by addition thereto of an alkali or alkaline earth metal hydroxide, such as caustic or potassium hydroxide, at a strength, for example, ranging from 3 to 6 percent of caustic. For convenience, the extraction into the aqueous phase can take place at elevated temperature, for example, in a hot aqueous phase. Illustratively, the extraction into the aqueous phase can be carried out by heating the system from room temperature up to 90° C. with agitation.

The pyrrole-2-acetic acid is converted to its alkali or alkaline earth metal salt and extracted into the aqueous phase. The phases are then separated and the organic phase containing additional impurities is then discarded.

By means of this transfer from the aqueous to the organic phase and back to the aqueous phase, numerous water-and organic-soluble impurities are easily removed from the pyrrole-2-acetic acid product and the materials handling operations are accomplished in liquid form avoiding the difficulties and losses involved in filtration and solids handling.

The aqueous phase containing the product pyrrole is then contacted with a decolorizing agent. Several commercial decolorizing agents are known and include charcoal, bone char, activated carbon, various clays, alumina and the like. The preferred decolorizing agents are selected from charcoal, bone char and activated carbon, with charcoal being most highly preferred. The decolorized aqueous solution containing the desired 1-$R_5$-4-$R_4$-5-aroylpyrrole-2-acetic acid salt is then recovered for final purification by recrystallizing from a suitable liquid.

In accord with the present invention, the process can be more particularly illustrated in the following manner. A substituted pyrrole compound, such as 1,4-dimethyl-5-p-chlorobenzoylpyrrole-2-acetic acid, as a crude aqueous solution from the previously known prior art steps of acylation of the ethyl 1,4-dimethylpyrryl-2-acetate with p-chlorobenzoyl chloride in the presence of a Friedel-Crafts catalyst followed by saponification with excess caustic and acidification with concentrated mineral acid to obtain the acid form of the desired product, is extracted with a mixture of an aromatic hydrocarbon compound and a lower alkanol, such as specifically a mixture of 90 weight percent xylene and 10 weight percent ethanol with agitation at 90° C. The organic and aqueous phases are separated and the organic phase containing the 1,4-dimethyl-5-p-chlorobenzoylpyrrole-2-acetic acid is carried forward while the aqueous phase containing water-soluble impurities is treated or discarded. The organic phase is then treated with aqueous caustic at 90° C. with agitation to convert the substituted pyrrole acid to its salt form and is extracted into the aqueous phase, leaving organic-soluble impurities in the organic phase. The phases are separated and the organic phase is treated for disposal. The aqueous phase containing the desired product is agitated with a decolorizing agent, such as charcoal, at about 90°-95° C. for a period sufficient to decrease the color of the aqueous solution. Recovery of the final product from aqueous solution can be carried out by recrystallization techniques well known in the art as especially applied to this particular product. Thus, for example, the aqueous phase can be filtered to remove the decolorizing agent, cooled to crystallize the sodium 1,4-dimethyl-5-p-chlorobenzoylpyrrole-2-acetic acid salt and the crystals collected, for instance by filtration, for drying and formulation into the final unit dosage form. Other recovery techniques may also be employed.

If the starting crude aqueous solution is especially dark, the extractions indicated may be repeated one or more times, as required to obtain the desired degree of product enhancement before final recovery. For example, the requirement for additional extractions can be determined by the appearance of the solution prior to decolorization. If the solution has an amber color, it is suitable for decolorization; however, if the solution is a dark reddish-brown in color, additional extraction steps should be carried out. This visual approach is necessary because convenient analytical techniques, such as vapor phase chromatographic analysis have not been useful in identifying the color-forming materials.

The process of the present invention is more clearly illustrated by reference to the following examples.

EXAMPLES 1-3

A crude aqueous solution of 1,4-dimethyl-5-p-chlorobenzoylpyrrole-2-acetic acid was extracted into a mixture of 90 weight percent xylene and 10 weight percent ethanol using the proportions of 128 moles of xylene per mole of the pyrrole compound and 33 moles of ethanol per mole of pyrrole compound by agitation at 90° C. for 30 minutes. The agitation was stopped, the phases settled and the lower aqueous phase was drained from the extraction vessel. Then a dilute (3 weight percent) caustic solution was added to the extraction vessel, 5 moles of sodium hydroxide per mole of pyrrole compound and 350 moles of water per mole of pyrrole compound, and the pyrrole compound was converted into the sodium salt by agitation at 90° C. for 30 minutes and extracted into the aqueous phase. The agitation was stopped and the organic phase was removed. Then activated carbon was added to the aqueous pyrrole salt solution and agitated for 30 minutes at 90°-95° C. The results of several experiments are given in the table below. In Example 3, the xylene-ethanol extraction was carried out twice because of the dark color of the starting solutions.

TABLE

| Example No. | Number of Xylene-Ethanol Extractions | Amount of Activated Carbon (g/g Pyrrole) | Yield of Pyrrole Salt (%) | Color |
|---|---|---|---|---|
| 1 | 1 | 0.71 | 83 | Good |

TABLE-continued

| Example No. | Number of Xylene-Ethanol Extractions | Amount of Activated Carbon (g/g Pyrrole) | Yield of Pyrrole Salt (%) | Color |
|---|---|---|---|---|
| 2 | 1 | 0.38 | 82 | Good |
| 3 | 2 | 0.33 | 80 | Good |

Having disclosed the process of the present invention, one skilled in the art can readily envision variations, modifications and changes within the scope and spirit of this invention. Therefore, it is desired that the present invention be limited only by the lawful scope of the following claims.

What is claimed:

1. A process for preparing a substituted pyrrole compound of the formula

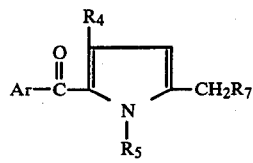

wherein the foregoing formula, said $R_4$ and $R_5$ each are independently selected from loweralkyl, and said $R_7$ is COOM in which M is an alkali metal, and Ar is selected from phenyl, thienyl, 5-methylthienyl, monosubstituted phenyl and polysubstituted phenyl, each substituent of said substituted phenyls being a member selected from the group consisting of halo, loweralkyl, trifluoromethyl, loweralkoxy, nitro, amino, cyano and methylthio, which comprises the steps of (a) contacting a crude aqueous mixture containing a 1-$R_5$-4-$R_4$-5-aroyl-pyrrole-2-acetic acid with a mixed organic extractant therefor said mixed organic extractant comprising a mixture of an organic hydrocarbon compound selected from benzene, xylene, and toluene and a lower alkanol selected from methanol, ethanol and propanol so that the pyrrole is extracted into the organic phase, (b) separating the phases, (c) treating the organic phase with a basic aqueous extractant selected from an aqueous alkali metal or alkaline earth metal hydroxide so that the pyrrole salt formed is extracted into the aqueous phase, (d) separating the phases, (e) contacting the pyrrole with a decolorizing agent and (f) recovering the resulting substituted pyrrole compound of the general formula above.

2. The process of claim 1 wherein said step (a) said mixed organic extractant is a mixture of xylene and ethanol.

3. The process of claim 1 wherein said mixed organic extractant contains from about 75 to about 95 percent by weight of said organic hydrocarbon compound and from about 5 to about 25 percent by weight of said lower alkanol.

4. The process of claim 1 wherein the treatment of said step (c) is carried out at elevated temperature.

5. The process of claim 1 in which said basic aqueous extractant is an aqueous alkali metal hydroxide selected from aqueous sodium hydroxide and aqueous potassium hydroxide.

6. The process of claim 1 in which said basic aqueous extractant is aqueous caustic which ranges in concentration of from 3 to 6 percent by weight.

7. The process of claim 1 wherein said step (e) said decolorizing agent is selected from charcoal, bone char and activated carbon.

8. The process of claim 7 wherein said step (e) said contacting is carried out at elevated temperature.

9. The process of claim 1 wherein said step (f) is further characterized by recrystallizing said pyrrole from water.

10. The process of claim 1 further characterized by after said step (d) acidifying the separated aqueous phase with a strong acid to obtain the acetic acid form of said pyrrole employed in step (a) and repeating steps (a) through (d) before decolorizing and recovering said substituted pyrrole compound.

* * * * *